(12) United States Patent
Yamamoto et al.

(10) Patent No.: US 6,924,103 B2
(45) Date of Patent: Aug. 2, 2005

(54) SCREENING METHOD FOR GENE VARIATION

(75) Inventors: Nobuko Yamamoto, Kanagawa (JP); Tadashi Okamoto, Kanagawa (JP); Shinya Tanaka, Tokyo (JP); Tomohiro Suzuki, Kanagawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/942,588

(22) Filed: Aug. 31, 2001

(65) Prior Publication Data

US 2002/0106667 A1 Aug. 8, 2002

(30) Foreign Application Priority Data

Aug. 31, 2000 (JP) ........................................ 2000-263396

(51) Int. Cl.[7] ........................... C12Q 1/68; C07H 21/04
(52) U.S. Cl. ...................... 435/6; 435/287.2; 536/24.3
(58) Field of Search ........................... 435/6, 7.1, 91.1, 435/91.2, 287.2; 536/221, 23.1, 24.3–33

(56) References Cited

U.S. PATENT DOCUMENTS

| 5,202,231 | A |   | 4/1993  | Drmanac et al.     | 435/6    |
| 5,445,934 | A |   | 8/1995  | Fodor et al.       | 435/6    |
| 5,733,729 | A |   | 3/1998  | Lipshutz et al.    | 435/6    |
| 6,027,880 | A |   | 2/2000  | Cronin et al.      | 435/6    |
| 6,306,643 | B1| * | 10/2001 | Gentalen et al.    | 435/287.2|
| 6,309,823 | B1| * | 10/2001 | Cronin et al.      | 435/6    |
| 6,309,824 | B1| * | 10/2001 | Drmanac            | 435/6    |

FOREIGN PATENT DOCUMENTS

| EP | 0 717 113 A2 | 6/1996 |
| EP | 0 967 291 A1 | 12/1999 |
| EP | 0 995 804 A2 | 4/2000 |
| WO | WO 95/11995 | 5/1995 |

OTHER PUBLICATIONS

Gennady Yershov et al., "DNA Analysis and Diagnostics on Oligonucleotide Microchips," 93 *Proc. Natl. Acad Sci.* 4913–4918 (1996).

Dmitry Proudnikov et al., "Analysis of Mutations in Oral Poliovirus Vaccine by Hybridization with Generic Oligonucleotide Microchips," 28 *Biologicals* 57–66 (2000).

David G. Wang et al., "Large–Scale Identification, Mapping, and Genotyping of Single–Nucleotide Polymorphisms in the Human Genome," 280 *Science* 1077–1082 (1998).

Mark Chee et al., "Accessing Generic Information with High–Density DNA Arrays," 274 *Science* 610–614 (1996).

* cited by examiner

Primary Examiner—Kenneth R. Horlick
(74) Attorney, Agent, or Firm—Fitzpatrick, Cella, Harper & Scinto

(57) ABSTRACT

A method for screening presence or absence of a variation in a region of a nucleic acid which comprises the steps of (a) preparing a sample containing a test nucleic acid corresponding to the region, (b) preparing a probe having a base sequence fully complementary to a normal sequence of the region, and a plurality of probes each having at least one base not complementary to the normal sequence, (c) fixing the probes in separate regions on a surface of a substrate to prepare a DNA array substrate, (d) reacting the test nucleic acid with the probes on the DNA array substrate, (e) measuring signals in each region where the signals are originated from respective hybrids formed between the test nucleic acid and one of the probes, and (f) calling variation in the test nucleic acid using a pattern of total signals of all regions.

12 Claims, 7 Drawing Sheets

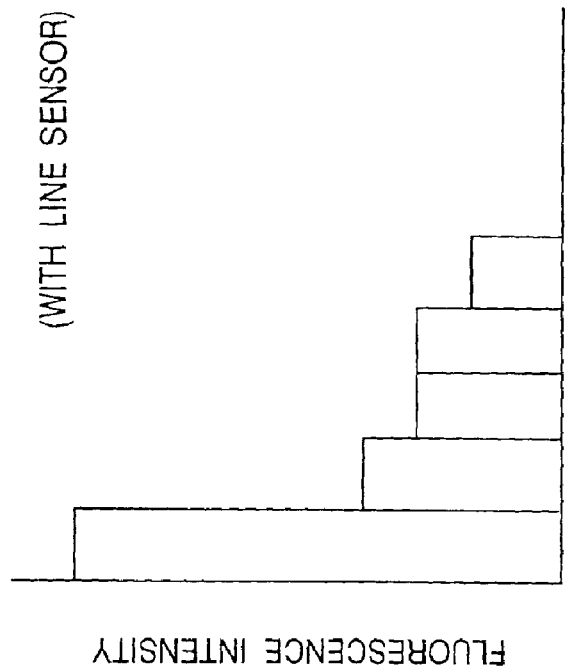
FIG. 1B (WITH LINE SENSOR)
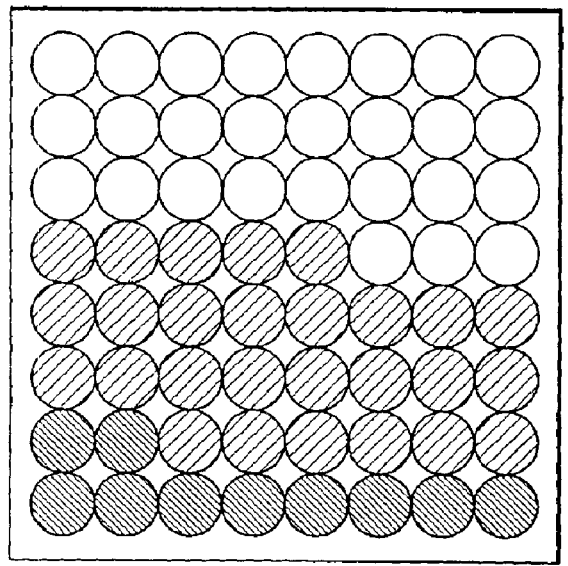
FIG. 1A
- ⬤ FULL MATCH OR ONE-BASE MISMATCH WITH NORMAL GENE
- ◐ TWO-BASE MISMATCH WITH NORMAL GENE
- ○ THREE-BASE MISMATCH WITH NORMAL GENE

FIG. 2

Top sequences (left to right):
GATGGGCCTCANGTTCAT
GATGGGCCTCGNGTTCAT
GATGGGCCTCCNGTTCAT
GATGGGCCTCTNGTTCAT
GATGGGTCTCANGTTCAT
GATGGGTCTCGNGTTCAT
GATGGGTCTCCNGTTCAT
GATGGGTCTCTNGTTCAT Grid (rows labeled A G C T | A G C T; columns as shown):

| | A | G | C | T | A | G | C | T |
|---|---|---|---|---|---|---|---|---|
| | 1 | 2 | 3 | 4 | 33 | 34 | 35 | 36 |
| | 5 | 6 | 7 | 8 | 37 | 38 | 39 | 40 |
| | 9 | 10 | 11 | 12 | 41 | 42 | 43 | 44 |
| | 13 | 14 | 15 | 16 | 45 | 46 | 47 | 48 |
| | 17 | 18 | 19 | 20 | 49 | 50 | 51 | 52 |
| | 21 | 22 | 23 | 24 | 53 | 54 | 55 | 56 |
| | 25 | 26 | 27 | 28 | 57 | 58 | 59 | 60 |
| | 29 | 30 | 31 | 32 | 61 | 62 | 63 | 64 |

Bottom sequences (left to right):
GATGGGACTCANGTTCAT
GATGGGACTCGNGTTCAT
GATGGGACTCCNGTTCAT
GATGGGACTCTNGTTCAT
GATGGGCTCANGTTCAT
GATGGGCTCGNGTTCAT
GATGGGCTCCNGTTCAT
GATGGGCTCTNGTTCAT

FIG. 4
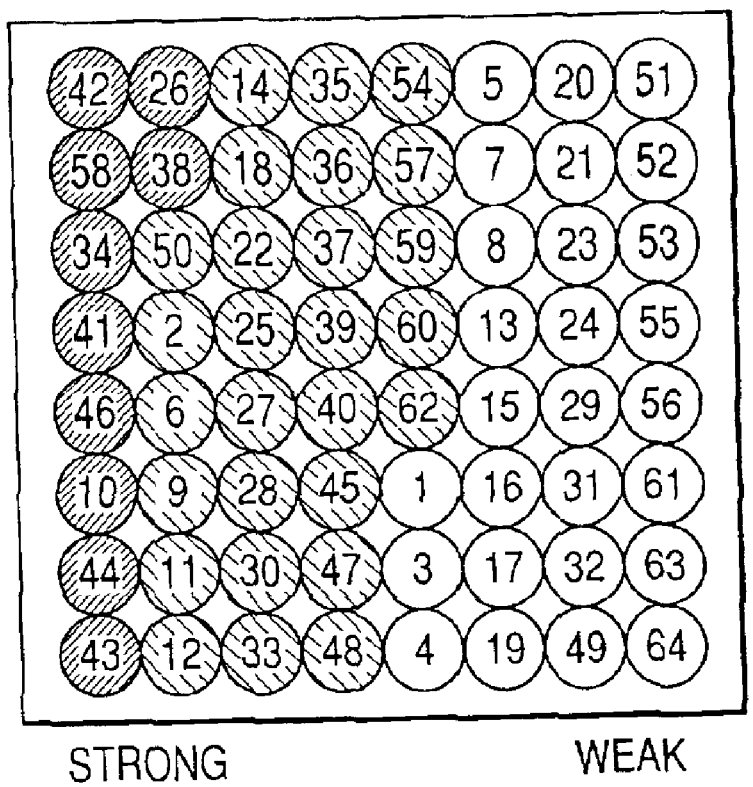
 FULL MATCH OR ONE-BASE MISMATCH WITH NORMAL GENE
 TWO-BASE MISMATCH WITH NORMAL GENE
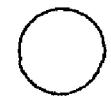 THREE-BASE MISMATCH WITH NORMAL GENE

FIG. 9
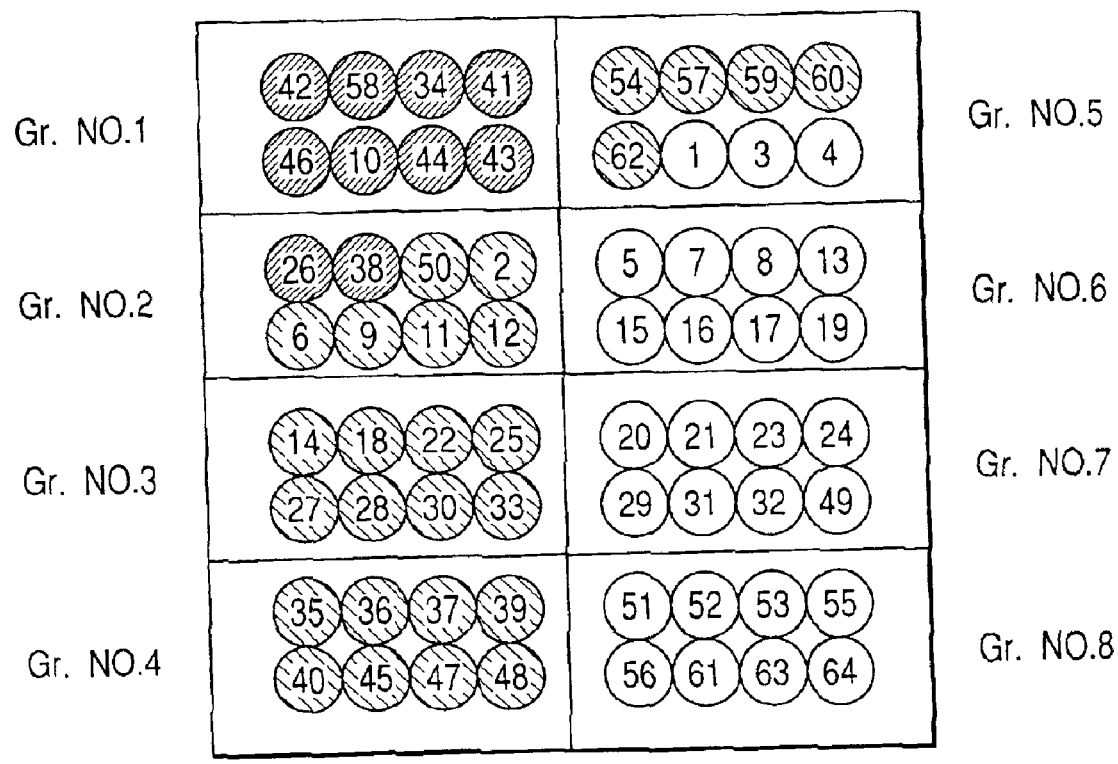
Gr. NO.1 Gr. NO.5
Gr. NO.2 Gr. NO.6
Gr. NO.3 Gr. NO.7
Gr. NO.4 Gr. NO.8
 FULL MATCH AND ONE-BASE MISMATCH WITH NORMAL GENE
 TWO-BASE MISMATCH WITH NORMAL GENE
 THREE-BASE MISMATCH WITH NORMAL GENE

SCREENING METHOD FOR GENE VARIATION

BACKGROUND OF INVENTION

1. Field of the Invention

The present invention relates to a variation detection method and a system for it useful for screening of a gene variation etc.

2. Related Background Art

One of the techniques for sequencing nucleic acid etc. or for detecting the sequence is to utilize a DNA array. U.S. Pat. No. 5,445,934 discloses a DNA array where 100,000 or more oligonucleotide probes are bonded in 1 inch square. Such a DNA array has an advantage that many characteristics can be examined at the same time with a very small sample amount. When a fluorescence-labeled sample is poured onto such a DNA chip, DNA fragments in the sample bind to probes having a complementary sequence fixed on the DNA chip, and only that part can be discriminated by fluorescence to elucidate the sequence of the DNA fragment in the DNA sample.

Sequencing By Hybridization (SBH) is a method for examining the base sequence utilizing such a DNA array and the details are described in U.S. Pat. No. 5,202,231. In the SBH method, all possible sequences of an oligonucleotide of a certain length are arranged on the substrate, then fully matched hybrids formed by hybridization reaction between probes and the sample DNA are detected. If a set of fully matched hybrids is obtained, the set will give an assembly of overlapping sequences with one base shift being a part of one certain sequence, which sequence is extracted for calling.

Including the SBH method, when complementariness between an oligonucleotide and a sample DNA is examined, it is very difficult to call whether a hybrid was formed or not using one probe for one test item, since the stability of a hybrid differs sequence to sequence, and there is no perfect signal for calling the full complementariness. Science vol. 274 p.610–614, 1996 discloses a method for calling by comparing the signal intensity of a perfect match hybrid and the weaker intensities of one-base mismatch hybrids. In this method, 15-mer oligonucleotide probes, differing from each other only by one mismatching base at the center of the sequence, are prepared, and the fluorescence intensities of the hybrids of the probes are compared. When the intensity of the full matched hybrid is stronger than that of other hybrids by a predetermined rate, it is called positive.

Further, U.S. Pat. No. 5,733,729 discloses a method using a computer to differentiate a base sequence of a sample from a comparison of fluorescence intensities of obtained hybrids for more accurate calling.

However, the actual binding strength of a hybrid depends on the GC content etc., and difference of the fluorescence intensity between a full match hybrid and a one-base mismatch hybrid also varies in a considerable range depending on the sequence. Thus, a method for calling whether a sequence is fully complementary to a probe or not, using a 15 mer oligonucleotide probe to compare it with other three probes having one mismatched base at the center thereof, can provide more accuracy if each stability is evaluated theoretically or empirically before comparison.

In addition, accurate calling requires precise quantification of signals, and therefore, precision apparatuses such as a confocal laser microscope. Furthermore, in order to measure the fluorescence intensity of a hybrid of every probe and to determine the gene sequence by analyzing the data, a large-scale computer apparatus as well as a detection apparatus for reading the arrays are further required. Therefore, this is a big obstacle for ready use of the DNA array.

On the other hand, gene diagnosis using such a DNA array may be used in group medical examination, individual gene examination or gene-polymorphism study. In such a case, however, the above described precise measurement and analysis are not always required, where a large amount of samples are rapidly treated at a low cost in order to find out variated samples concerning a specific item from a large number of normal samples. Further, the precision apparatus and analysis as described above will be expensive. Accordingly, a concept that screening of the presence or absence of a variation is first performed, and then, detailed examinations of the samples suspected of variation are carried out by screening, saving both time and cost.

SUMMARY OF THE INVENTION

One object of the present invention is to provide a method suitable for mass screening so as to determine rapidly the presence or absence of a gene variation without need of an expensive apparatus and a complex analysis.

The present invention provides a DNA array in which a group of probes which will give strong signals forming hybrids with a normal gene sequence, and a group of probes having sequences expected to form hybrids with gene variants are separately arranged, on the premise that the base sequence of a normal gene and those of variants have already been established. Furthermore, the above described object is achieved by providing a detection method using such an array.

According to one aspect of the present invention, there is provided a method for screening of the presence or absence of variation in a region of a nucleic acid comprising the steps of:

(a) preparing a test nucleic acid corresponding to the region;

(b) preparing a probe having a base sequence fully complementary to a normal sequence of the region, and a plurality of probes each having at least one base not complementary to the normal sequence;

(c) fixing the probes in separate regions on a surface of a substrate to prepare a DNA array substrate;

(d) reacting the test nucleic acid with the probes on the DNA array substrate;

(e) measuring signals in each region totally where the signals are originated from respective hybrids formed between the test nucleic acid and one of the probes; and (f) determining the presence or absence of mutation in the test nucleic acid comparing with a histogram pattern of signals of all regions obtained using a normal sample without variation.

According to another aspect of the invention, there is provided a DNA array substrate for screening a variation in a region of a nucleic acid, wherein a full match probe fully complementary to a normal sequence of the region, and a plurality of mismatch probes having at least one base mismatch to the sequence are arranged on the substrate; and the probes are arranged to form at least two separate regions selected from:

a first region containing at least one probe which provides a signal of a certain intensity on reaction with a nucleic acid having the normal sequence, a second region containing at least one probe which provides a weaker signal than the probe of the first region on reaction with a nucleic acid having normal sequence, and the third region containing at least one probe which provides no signal on reaction with a nucleic acid having normal sequence.

According to still another aspect of the present invention, there is provided a system for detecting variation comprising a DNA array substrate as described above and a signal measuring apparatus which measures signals from separate regions of the DNA array substrate.

The present invention can provide a method suitable for mass screening, so as to rapidly determine only the presence or absence of a gene variant, without need of an expensive apparatus and complex analysis.

BRIEF DESCRIPTION OF THE DRAWINGS

FIG. 1A is a schematic example of arrangement of separate regions on a DNA array substrate, and FIG. 1B shows a histogram of fluorescence intensities (pattern) corresponding to separate regions of the above arrangement, measured using a line sensor;

FIG. 2 shows an arrangement of 64 types of DNA probes;

FIG. 4 shows normal fluorescence intensities obtained by hybridization where Gr. NO. denotes group number;

FIG. 9 shows normal fluorescence intensities obtained by hybridization where Gr. NO. denotes group number.

DETAILED DESCRIPTION OF THE INVENTION

Figure 3:
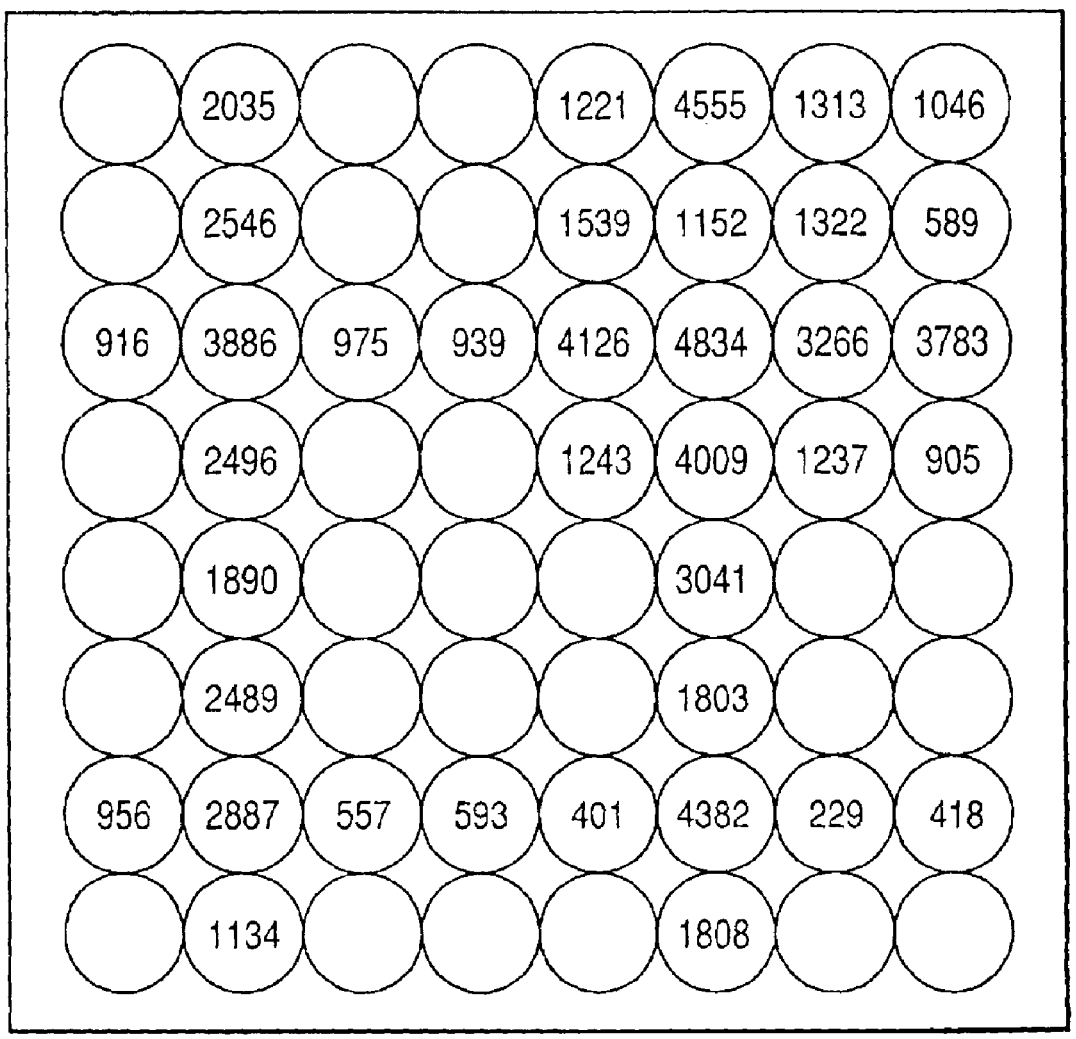
FIG. 3 shows a pattern of the fluorescence intensities obtained by hybridization.

The present invention provides a screening method for gene variants using a DNA array in which a group of probes which will give strong signals forming hybrids with a normal gene sequence, and a group of probes having sequences expected to form hybrids with gene variants are separately arranged, on the premise that the base sequence of a normal gene and those of variants have already been established. Furthermore, the above described object is achieved by providing a detection method using such an array.

Here, the present invention will be described in detail with examples where signals from the separate regions are fluorescence. However, signals in the present invention are not limited to fluorescence but may be other light signals or electric signals.

Binding strength between single-stranded nucleic acids to form a hybrid is controlled by various factors, and when a probe having a length of about 12 mer to 25 mer is used, it is practically difficult to perfectly exclude hybrids having one-base mismatches.

When the signal of the hybrid to be detected is a light such as fluorescence, the following phenomena are observed. Fluorescence stability of a hybrid having two mismatches (two-base mismatch hybrids) is much lower than that of the one-base mismatched hybrid, regardless of positions, continuity or discontinuity of the mismatched bases. On the other hand, signal from a three-base mismatch hybrid is hardly observed. However, one-base mismatch hybrids may have more than 50% signal intensity of a full match hybrid. Thus, when a sample is a nucleic acid of normal sequence, strong fluorescence is observed in a region where a full match probe and probes having one mismatching base have been arranged, while the fluorescence intensity in a region where hybrids of low stability are formed is almost zero. On the other hand, when a sample is a nucleic acid of a variant sequence, the probe fully complementary to the normal sample makes a mismatch hybrids with the sample. Thus the fluorescence is weaker at a region than that in case of the normal sample, at the same time, fluorescence from a full match hybrid and one-base mismatch hybrids with the sample appears in another region where low signals are expected in case of the normal nucleic acid. Accordingly, by comparing fluorescence histogram of the regions, it is possible to distinguish between the normal nucleic acid and the variant nucleic acid.

In the present invention, a DNA array substrate where probes are arranged in separate regions according to the fluorescence intensities of their hybrids with a normal nucleic acid is used for more accurate calling. First, hybridization reaction of the normal nucleic acid with each probe is performed, and based on the fluorescence intensities of the hybrids obtained, separate regions each containing probes corresponding to strong fluorescence, no fluorescence, and moderate (weak) fluorescence are located at predetermined positions on the substrate.

When performing a test on multiple items simultaneously, the substrate should be divided into areas for respective items. In each area, probes having full match and one-base mismatch sequences to the normal gene sequence are arranged in a region, which are expected to give high signals, and the other probes having more than two-base mismatch are arranged in a separate region depending on the items. Thus we can discriminate normal test samples from variated ones.

The arrangement can be determined according to the type of the sensor to be used. For example, when a line sensor is used, each region is arranged from the left to right in the substrate in order of the strength of fluorescence obtainable by hybridization with the normal nucleic acid. Thus, the fluorescence intensity will be maximum in the left, then gradually decrease and come to zero in several regions in the right of the substrate. When an area sensor is used, it is necessary to evaluate the fluorescence quantity of at least two separate regions containing a group of probes which will provide the maximum fluorescence and a group of probes which will not provide any fluorescence respectively.

This will be described more specifically.

In the present invention, for example, whether a gene is normal or not can be called by providing a region containing a probe that forms a hybrid with a normal nucleic acid and the other region containing probes that form hybrids with variant genes separately on a DNA array, and taking a ratio of the signal from a hybrid corresponding to the normal nucleic acid and to the signals from hybrids corresponding to variant genes.

However, because one-base mismatched hybrids sometimes have strong signals, it is difficult to detect variation in the test sample when a DNA array where only probes being full match or one-base mismatch to a normal sequence are arranged is used. It is important that probes having two-base mismatch to the normal nucleic acid is present in the DNA array, which might be one-base mismatch probes to the test sample to form hybrids having strong signals.

Therefore, in the present invention, in order to judge more accurately, a preferable method is as follows. Probes having full match and one-base mismatch sequences to the normal nucleic acid sequence, which most samples in mass screening have, are arranged in a specified region on a DNA array substrate. In addition, probes having two- or three-base mismatch are arranged in a region different from the above region for high stability hybrids. Then, a hybridization reaction is performed with the normal nucleic acid or a sample, using the DNA array substrate of such an arrangement. Then the total of signals for each separate region is measured, and a pattern obtained with a sample nucleic acid is compared that with the normal nucleic acid are compared to determine the presence or absence of variation.

For example, when 64 probes (4×4×4=64) where different bases are arranged at three positions in 18 base length (Table 1, 5'-terminus is on the left) are used supposing that variation occurs at these three points, for any sample there should be present a probe fully complementary to the sample, nine one-base mismatch probes, 27 two-base mismatch probes and 27 three-base mismatch probes. Furthermore, it is relatively easy to set conditions of the hybridization reaction such that fluorescence is observed with the full match and one-base mismatch hybrids but not with three-base mismatch hybrids. Some two-base mismatch probes form hybrids and others not, depending to their sequences.

TABLE 1

| SEQ ID NO: | Sequence |
|---|---|
| 1 | GATGGGACTCAAGTTCAT |
| 2 | GATGGGACTCAGGTTCAT |
| 3 | GATGGGACTCACGTTCAT |
| 4 | GATGGGACTCATGTTCAT |
| 5 | GATGGGACTCGAGTTCAT |
| 6 | GATGGGACTCGGGTTCAT |
| 7 | GATGGGACTCGCGTTCAT |
| 8 | GATGGGACTCGTGTTCAT |
| 9 | GATGGGACTCCAGTTCAT |
| 10 | GATGGGACTCCGGTTCAT |
| 11 | GATGGGACTCCCGTTCAT |
| 12 | GATGGGACTCCTGTTCAT |
| 13 | GATGGGACTCTAGTTCAT |
| 14 | GATGGGACTCTGGTTCAT |
| 15 | GATGGGACTCTCGTTCAT |
| 16 | GATGGGACTCTTGTTCAT |
| 17 | GATGGGGCTCAAGTTCAT |
| 18 | GATGGGGCTCAGGTTCAT |
| 19 | GATGGGGCTCACGTTCAT |
| 20 | GATGGGGCTCATGTTCAT |
| 21 | GATGGGGCTCGAGTTCAT |
| 22 | GATGGGGCTCGGGTTCAT |
| 23 | GATGGGGCTCGCGTTCAT |
| 24 | GATGGGGCTCGTGTTCAT |
| 25 | GATGGGGCTCCAGTTCAT |
| 26 | GATGGGGCTCCGGTTCAT |
| 27 | GATGGGGCTCCCGTTCAT |
| 28 | GATGGGGCTCCTGTTCAT |
| 29 | GATGGGGCTCTAGTTCAT |
| 30 | GATGGGGCTCTGGTTCAT |
| 31 | GATGGGGCTCTCGTTCAT |
| 32 | GATGGGGCTCTTGTTCAT |
| 33 | GATGGGCCTCAAGTTCAT |
| 34 | GATGGGCCTCAGGTTCAT |
| 35 | GATGGGCCTCACGTTCAT |
| 36 | GATGGGCCTCATGTTCAT |
| 37 | GATGGGCCTCGAGTTCAT |
| 38 | GATGGGCCTCGGGTTCAT |
| 39 | GATGGGCCTCGCGTTCAT |
| 40 | GATGGGCCTCGTGTTCAT |
| 41 | GATGGGCCTCCAGTTCAT |
| 42 | GATGGGCCTCCGGTTCAT |
| 43 | GATGGGCCTCCCGTTCAT |
| 44 | GATGGGCCTCCTGTTCAT |
| 45 | GATGGGCCTCTAGTTCAT |
| 46 | GATGGGCCTCTGGTTCAT |
| 47 | GATGGGCCTCTCGTTCAT |
| 48 | GATGGGCCTCTTGTTCAT |
| 49 | GATGGGTCTCAAGTTCAT |
| 50 | GATGGGTTCTAGGTTCAT |
| 51 | GATGGGTCTCACGTTCAT |
| 52 | GATGGGTCTCATGTTCAT |
| 53 | GATGGGTCTCGAGTTCAT |
| 54 | GATGGGTCTCGGGTTCAT |
| 55 | GATGGGTCTCGCGTTCAT |
| 56 | GATGGGTCTCGTGTTCAT |
| 57 | GATGGGTCTCCAGTTCAT |
| 58 | GATGGGTCTCCGGTTCAT |
| 59 | GATGGGTCTCCCGTTCAT |
| 60 | GATGGGTCTCCTGTTCAT |
| 61 | GATGGGTCTCTAGTTCAT |
| 62 | GATGGGTCTCTGGTTCAT |
| 63 | GATGGGTCTCTCGTTCAT |
| 64 | GATGGGTCTCTTGTTCAT |

When these 64 probes are grouped into every eight probes in order of the fluorescence intensity obtained by hybridization with the normal nucleic acid (hereinafter "fluorescence intensity of a probe(s)" means expected intensity of a hybrid of the probe with a nucleic acid of normal sequence, if not otherwise stated), the total fluorescence intensity of the first group should be extremely high and the total fluorescence quantity of the sixth, seventh and eighth groups should be zero. Such classification by the fluorescence intensity may be performed empirically or theoretically through calculations.

Then, the hybridization reaction is performed in an actual system and the total quantity of fluorescence is determined for each classified group. Particularly, the fluorescence quantities of the sixth, seventh and eighth groups are important. Normally, fluorescence is not expected for these groups. When fluorescence is detected unexpectedly for these groups, it is understood that the sample is not normal but having variation at a part of the sequence. When the fluorescence is not detected for these groups, most of the sequences are normal.

For more accuracy, however, it is necessary to compare the fluorescence quantity of the first group with a normal case. When the fluorescence quantity is significantly lower than that expected for normal sequence, base variation is suspected. Further the histogram of the fluorescence intensity in the regions having medium fluorescence intensity, i.e. the second, third and fourth groups, should be compared with that of the normal one.

For more effective detection of variation, one may consider a method wherein the probes are arranged in order of signal intensity, that is, lined in the order of sequences of full match, one-base mismatch, two-base mismatch, and three-base mismatch to the normal sequence from one end, so that signal intensity may be zero in the region opposite to the region where the full match probe is placed. In this case, the total distribution pattern of the fluorescence intensity is examined. For example, when using an arrangement of the separate regions shown in FIG. 1A (one column corresponds to one separate region), a monotonously decreasing pattern as shown in FIG. 1B is obtained for the normal case while patterns having peaks in the intermediate regions will be obtained with variants.

The above arrangement method is similarly used for the case where the probes for multi-item testing are arranged on the same substrate. For each item, first, the full matched probe (to the normal sequence), then one-base mismatched sequences, two-base mismatched sequences and so on are placed in order of the strength of fluorescence intensity expected.

Such concept is universally applicable to any number of variation, not limited to the above method where the variation for only three bases is tested.

In addition, while we explained the cases where the signals can be obtained when the hybrids are formed, the method may be set such that signals are not obtained when the hybrids are formed, and obtained when the hybrids are not formed, depending on the signal generating system.

The sample nucleic acid can be prepared by extracting from the gene to be tested according to the necessity. The control normal nucleic acid can be synthesized on the basis of the known sequence.

The length of the probe fixed to the substrate is not limited so long as it is suitable for detection, for example, preferably 8 mer to 30 mer, more preferably 12 mer to 25 mer.

Probes may be fixed to the substrate by various methods, but droplet application by the ink jet method is preferably used in order to arrange spots of fixed probes with high efficiency, high density and high speed.

Each spot in the separate region is preferably 70 to 100 µm in diameter and spaced not to connect each other.

The spot number in each region is set so that the spots expected to have high fluorescence intensity can be measured together and the spots expected to have no fluorescence can be measured together, considering the constitution of the sensor.

A system for detecting variation of the present invention comprises a DNA array substrate wherein plural separate regions are arranged in a prescribed arrangement, and a sensor for measuring the signals in the separate regions subjected to measurement. In addition, for calling the presence or absence of variation using the DNA array substrate where the plural separate regions are provided, the signals from all separate regions may be detected and the results are used for calling the presence or absence of variation or, as a simpler method, signals may be compared between certain regions selected so as to detect the presence or absence of variation.

Computer analysis is conveniently performed connecting a computer system to the detection system. For many variants of a gene sequence, histogram patterns of signal intensity are prepared and stored in the computer, which helps the determination of variant easily and correctly.

As the sensor for signal detection, different types of photodiodes (e.g. Hamamatsu Photonics K.K.-made) are used. For example, some of the divided type silicon photodiode arrays can be used as both line sensor and area sensor. Particularly, those having a photo-receiving face of 1 to 2 mm×(2 to 3) mm are suitably used.

EXAMPLES

The present invention will be described in more detail referring to Examples below. Herein, "%" means "weight %".

Example 1
Preparation of DNA Array for Detection of Variant Gene for Line Sensor
1) Preparation of DNA Array Linked with 64 Types of Probes
(1) Probe Design It is well known that in the base sequence CGGAGG corresponding to the AA248 and AA249 of the tumor suppressor gene p53, frequently observed variation is those the first C to T, the second A to G for AA248, and the third G to T for AA249. Accordingly, aiming at these three positions, 64 types of probes were designed.

That is, the designed nucleic acid are 18-mer nucleic acids harboring variegated above mentioned six bases sandwiched between the common sequences, represented by 5'ATGAACNNGAGNCCCATC3' (SEQ ID NO: 68) where N corresponds to any of 4 bases, A, G, C and T. Actual probes to detect the above sequence should be have a complementary sequence of 5'GATGGGNCTCNNGT-TCAT3' (SEQ ID NO: 69).

FIG. 2 shows an arrangement of 64 types of DNA probes on a substrate. A sequence 5' ATGAACCGGAGGC-CATC3' (SEQ ID NO: 65) corresponding to the normal gene is expected to form a hybrid with DNA of probe 42 of 5'GATGGGCCTCCGGTTCAT3' (SEQ ID NO: 42) positioned at the third from the right and the third from the top.
Substrate Cleaning A glass plate of 1 inch square was placed in a rack and soaked in an ultrasonic cleaning detergent overnight. Then, after 20 min of ultrasonic cleaning, the detergent was removed by washing with water. After rinsing the plate with distilled water, ultrasonic treatment was repeated in a container filled with distilled water, for additional 20 min. Then the plate was soaked in a prewarmed 1N sodium hydroxide solution for 10 min, washed with water and then distilled water.
Surface Treatment Then the plate was soaked in an aqueous solution of 1% silane coupling agent (product of Shin-Etsu Chemical Industry: Trade name KBM 603) at a room temperature for 20 min, thereafter nitrogen gas was blown on the both sides blowing off water to dryness. The silane coupling treatment was completed by baking the plate in an oven at 120° C. for 1 hour. Subsequently, 2.7 mg of EMCS (N-(6-maleimidocaproyloxy) succinimide: Dojin Company) was weighed and dissolved in a 1:1 solution of DMSO/ethanol (final concentration: 0.3 mg/ml). The glass substrate treated with the silane coupling agent was soaked in this EMCS solution for 2 hours to react the amino group of the silane coupling agent with the succimide group of EMCS. At this stage, the maleimide group of EMCS is transferred to the glass surface. After that, the glass plate was washed with ethanol, and dried with nitrogen gas to be used for a coupling reaction with DNA.
3. Coupling of DNA to the Substrate
Synthesis of 64 DNA Probes The 64 types of probe DNAs shown in Table 1 each having an SH group (thiol group) at the 5' terminus were synthesized by a standard method.
Ejection of DNA Probes Each DNA was dissolved in water and diluted with SG Clear (aqueous solution containing 7.5% of glycerin, 7.5% of urea, 7.5% of thiodiglycol and 1% of acetylenol EH), to a final concentration of 8 µM.

Then 100 µl of this DNA solution was filled into a nozzle of a BJ printer Head BC 62 (Canon) modified to eject a small amount, and to eject six solutions per head. Two heads were used at a time so that 12 types of DNAs could be ejected at once, and the heads were changed 6 times so that 64 spots of 64 types of DNAs were formed independently on the predetermined positions. Thus obtained was a DNA array in which separate regions were arranged in a predetermined manner. The pitch of spots was 200 μm and the area formed with 8×8 spots was about 2 mm×2 mm.

After that, the plate was left standing in a humidified chamber for 30 min for linking reaction of the probe DNA to the substrate.

2. Measurement of Fluorescence Intensity of 64 Hybrids with Normal p53 Sequence (1) Hybridization Reaction Blocking Reaction After completion of the reaction, the substrate was washed with a 1 M NaCl/50 mM phosphate buffer solution (pH 7.0) to wash out thoroughly the DNA solution on the glass surface. Then, this was soaked in an aqueous solution of 2% bovine serum albumin and allowed to stand for 2 hours to carry out a blocking reaction.

Preparation of Model Sample DNA

Rhodamine labeled DNA No. 1 (SEQ ID NO: 65) of the same length as the probes but having the normal sequence of p53 gene was prepared. The sequence is shown below and rhodamine is bonded to the 5' terminus. (Synthesis of model sample of DNA).

The labeled DNA No. 65 (single strand) having the normal sequence of p53 gene (complementary to No. 42) and the same length in the same region as the probe DNA was prepared. The sequence is as shown below where rhodamine (Rho) is bound to the 5'-terminal.

No. 65: 5'-Rho-ATGAACCGGAGGCCCATC-3' (SEQ ID NO: 65)

Reaction Condition of Hybridization

Two milliliters of 50 nM DNA solution of a model sample containing 100 mM NaCl was placed into a container containing the DNA array substrate for a hybridization reaction. Initially it was heated at 70° C. for 30 min, then the temperature of the incubator was lowered to 40° C. and the reaction was continue for 3 hours.

(2) Detection

Method

The detection was performed by connecting an image analysis processing apparatus, ARGUS (a product of Hamamatsu Photonics) to a fluorescence microscope (a product of Nicon).

(3) Result

Distribution of the fluorescence quantity on the substrate obtained is shown in FIG. 3.

Example 2

Preparation of DNA Array for Detection of Variant Gene for Line Sensor (1) Preparation of DNA Array for Detection of Variation In Tables 2 and 3, these 64 probes are grouped in every 8 probes in order of intensity based on the above described results. The fluorescence intensity of the first group should be extremely strong, and the total fluorescence quantity of the sixth, seventh and eighth groups should be zero.

TABLE 2

| Group No. | SEQ ID NO: | Type of Mismatch |
|---|---|---|
| 1 | 42 | Full mismatch |
|  | 58 | One-base mismatch |
|  | 34 | One-base mismatch |
|  | 41 | One-base mismatch |
|  | 46 | One-base mismatch |
|  | 10 | One-base mismatch |
|  | 44 | One-base mismatch |
|  | 43 | One-base mismatch |

TABLE 2-continued

| Group No. | SEQ ID NO: | Type of Mismatch |
|---|---|---|
| 2 | 26 | One-base mismatch |
|  | 38 | One-base mismatch |
|  | 50 | Two-base mismatch |
|  | 2 | Two-base mismatch |
|  | 6 | Two-base mismatch |
|  | 9 | Two-base mismatch |
|  | 11 | Two-base mismatch |
|  | 12 | Two-base mismatch |
| 3 | 14 | Two-base mismatch |
|  | 18 | Two-base mismatch |
|  | 22 | Two-base mismatch |
|  | 25 | Two-base mismatch |
|  | 27 | Two-base mismatch |
|  | 28 | Two-base mismatch |
|  | 30 | Two-base mismatch |
|  | 33 | Two-base mismatch |
| 4 | 35 | Two-base mismatch |
|  | 36 | Two-base mismatch |
|  | 37 | Two-base mismatch |
|  | 39 | Two-base mismatch |
|  | 40 | Two-base mismatch |
|  | 45 | Two-base mismatch |
|  | 47 | Two-base mismatch |
|  | 48 | Two-base mismatch |

TABLE 3

| Group No. | SEQ ID NO: | Type of Mismatch |
|---|---|---|
| 5 | 54 | Two-base mismatch |
|  | 57 | Two-base mismatch |
|  | 59 | Two-base mismatch |
|  | 60 | Two-base mismatch |
|  | 62 | Two-base mismatch |
|  | 1 | Three-base mismatch |
|  | 3 | Three-base mismatch |
|  | 4 | Three-base mismatch |
| 6 | 5 | Three-base mismatch |
|  | 7 | Three-base mismatch |
|  | 8 | Three-base mismatch |
|  | 13 | Three-base mismatch |
|  | 15 | Three-base mismatch |
|  | 16 | Three-base mismatch |
|  | 17 | Three-base mismatch |
|  | 19 | Three-base mismatch |
| 7 | 20 | Three-base mismatch |
|  | 21 | Three-base mismatch |
|  | 23 | Three-base mismatch |
|  | 24 | Three-base mismatch |
|  | 29 | Three-base mismatch |
|  | 31 | Three-base mismatch |
|  | 32 | Three-base mismatch |
|  | 49 | Three-base mismatch |

TABLE 3-continued

| Group No. | SEQ ID NO: | Type of Mismatch |
|---|---|---|
| 8 | 51 | Three-base mismatch |
|   | 52 | Three-base mismatch |
|   | 53 | Three-base mismatch |
|   | 55 | Three-base mismatch |
|   | 56 | Three-base mismatch |
|   | 61 | Three-base mismatch |
|   | 63 | Three-base mismatch |
|   | 64 | Three-base mismatch |

Then, the surface of the substrate was separated into eight columns to arrange the first group, the second group and so on in order of intensity from the left to the right. Then, the probes were arranged at the positions of the corresponding probe numbers as shown in FIG. 4 using the ink jet method in the same manner is in Example 1 to prepare the DNA arrays for detecting variation. The lines composed of each group have intervals of 200 µm.

(2) Testing Normal Gene Using DNA Array

The hybridization reaction was carried out under the same conditions as in Example 1. Thereafter, the total fluorescence of each group was detected using a line sensor (S 272102: Hamamatsu Photonics K.K.-made).

Figure 5:
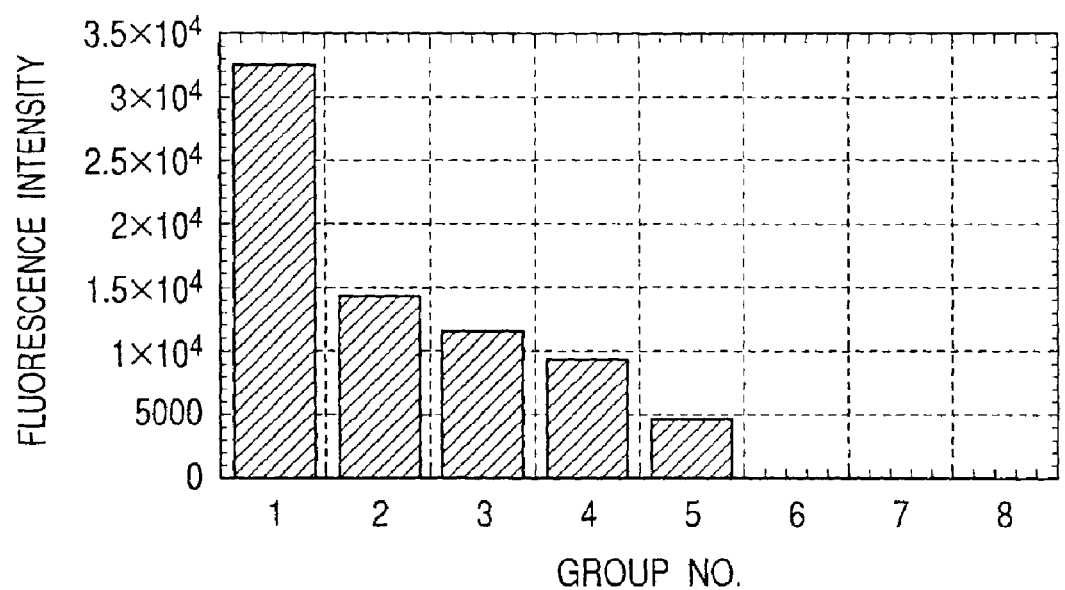
FIG. 5 is a distribution pattern of fluorescence intensities corresponding to the separate regions of the arrangement, measured using a line sensor.

The results are shown in FIGS. 4 and 5. The fluorescence of the first group was the highest and the intensity of the second group decreases below the half of that. Fluorescence was hardly observed in the sixth, seventh and eighth groups.

Example 3

Detection of Variant Gene Using DNA Array (1)

1. Synthesis of Model Variant DNA

The labeled DNA No. 66 having the same length as the probes and a sequence complementary to No. 46 probe that differs by one base from the normal sequence of p53 gene was prepared. The sequence is shown below. Rhodamine was bound to the 5'-terminal. The underlined part is the variant position.

No. 66: 5'-Rho-ATGAACCAGAGGCCCATC-3' (SEQ ID NO: 66)

Reaction Conditions for Hybridization

The hybridization reaction was carried out under the same conditions as in Example 1. The concentration of the model sample DNA was 50 nM.

Detection by Line Sensor

Figure 6:
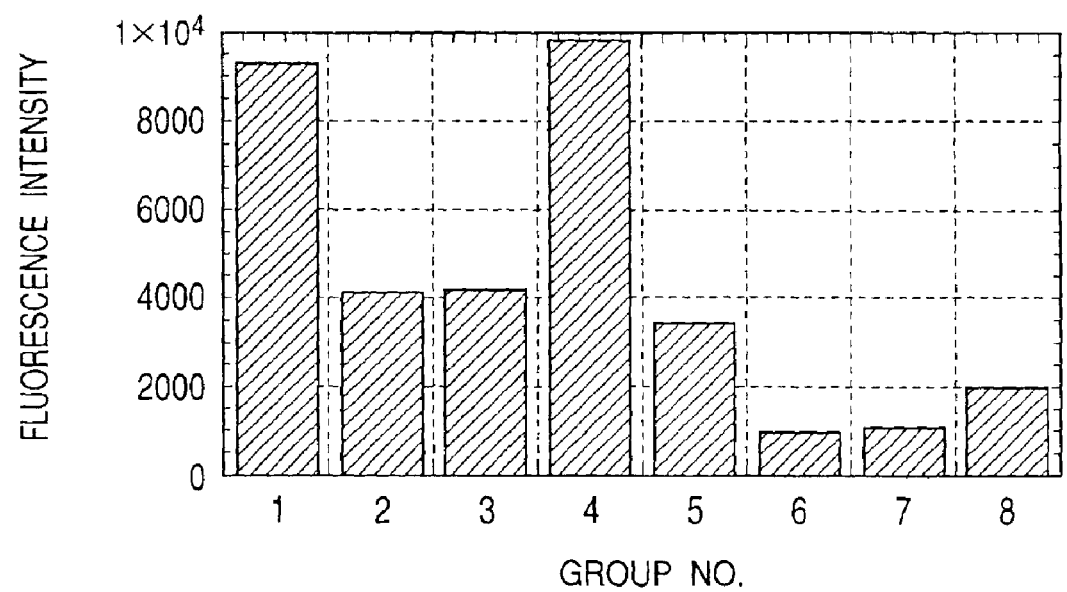
FIG. 6 is a distribution pattern of fluorescence intensities corresponding to the separate regions of the arrangement, measured using a line sensor.

After the hybridization reaction, the DNA array was evaluated in the same manner as in Example 2 using a line sensor. As shown in FIG. 6, the fluorescence was observed in the sixth, seventh and eighth groups where the fluorescence was not observed with the normal gene. Thus, it was easily judged that the sample gene was not normal. Further, since the fluorescence intensity was high at the first and the fourth groups corresponding to probe Nos. 35 to 48, it is inferred that they have the variation in the upper right quarter of FIG. 2 with a sequence very close to the normal gene.

This result shows that the screening method for variant genes of the present invention is extremely effective.

Example 4

Detection of Variant Gene Using DNA Array (2)

Figure 7:
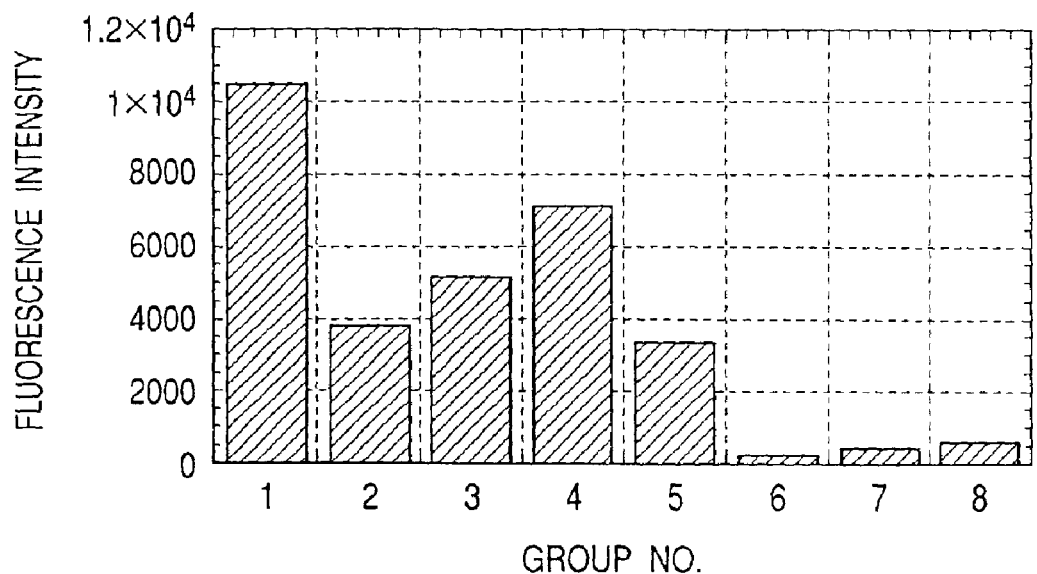
FIG. 7 is a distribution pattern of fluorescence intensities corresponding to the separate regions of the arrangement, measured using a line sensor.

The hybridization reaction was carried out under the same conditions as in Example 3, except that the concentration of the model target gene used for the hybridization reaction was changed to 5 nM. The result is shown in FIG. 7.

Since the results similar to Example 3 were obtained to show that the method of the present invention works not depending on the hybridization reaction conditions.

Example 5

Detection of Variant Gene Using DNA Array (3)

Synthesis of Variant Model Sample DNA

The labeled DNA No. 67 having the same length as the probes and a sequence complementary to No. 10 probe that differs by one base from the normal sequence of p53 gene was prepared. The sequence is as shown below where Rho represents rhodamine bound to the 5'-terminus. The underlined part is the variant position.

No. 67: 5'-Rho-ATGAACCGGAGTCCCATC-3' (SEQ ID NO: 67)

Hybridization Reaction

Figure 8:
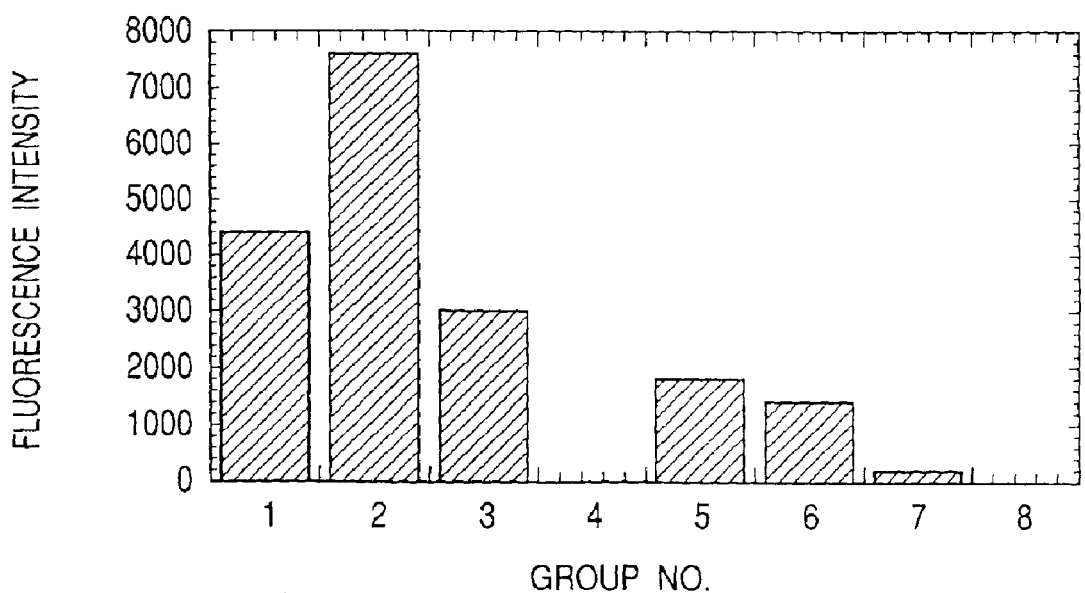
FIG. 8 is a distribution pattern of fluorescence intensities corresponding to the separate regions of the arrangement, measured using a line sensor.

The hybridization reaction was carried out under the same conditions as in Example 1 using the above variation model sample DNA. The concentration of the sample was 50 nM. The result is shown in FIG. 8.

Fluorescence was observed in the sixth and seventh groups which was not observed for the normal gene, showing that this was not a normal gene. Since the fluorescence in the second group was higher than in the first group which would be the highest for the normal gene, it is presumed that it has a variation included in the probe sequences of the second group (the upper left quarter in FIG. 2).

This result shows that the screening method for variant genes of the present invention is feasible not depending on the variation types.

Example 6

Preparation of DNA Array for Area Sensor

The probes grouped as shown in Example 2 were arranged by the ink jet method in the separate regions on the substrate as shown in FIG. 9 to prepare the DNA array for area sensor.

Then, the hybridization reaction was performed using the variant model sample used in Example 4. As a result, the fluorescence was observed in the sixth, seventh and eighth groups which was not observed for the normal gene, therefore, it was easily judged that this gene was a variant one.

What is claimed is:

1. A DNA array substrate for screening variation in a portion of a nucleic acid comprising:
   a first group of probes, each probe having a base sequence that hybridizes with a wild-type sequence of the portion to give a strong signal, and
   a second group of probes, each probe having a base sequence that is expected to hybridize with a gene variant but not with the wild-type sequence to give a strong signal;
   wherein each probe is fixed as a separate probe spot on a substrate to form at least two separate regions of probe spots selected from:
   a first region containing probes of the first group,
   a second region containing probes of the second group, each of which provides a weaker signal than the probes of the first region on reaction with the wild-type sequence, and
   a third region containing probes of the second group, each of which provides no signal on reaction with the wild-type sequence,
   wherein the probe spots are grouped such that each one of the regions contains probes not found in other regions.

2. The DNA array substrate according to claim 1, wherein the signal is fluorescence.

3. The DNA array substrate according to claim 1, wherein the signal is chemical luminescence.

4. The DNA array substrate according to claim 1, wherein the separate regions are arranged on the substrate in order of signal intensity obtainable by reacting with the wild-type sequence along a direction of a detection.

5. The DNA array substrate according to claim 1, wherein a length of the probes is 8 to 30 nucleotides.

6. The DNA array substrate according to claim 5, wherein the length of the probes is 12 to 25 nucleotides.

7. A system for detecting variation comprising a DNA array substrate according to claim 1 and a signal measuring apparatus which measures signals from separate regions of the DNA array substrate.

8. A method for detecting the presence of a target nucleic acid in a sample using an array substrate having plural probe spots arranged thereon to form an array, wherein said probe spots are arranged into groups such that each group contains probes not found in other groups, the method comprising the steps of:
   a) measuring a total signal intensity of a plurality of probe spots in one group integrally wherein the probes are in a hybridized state;
   b) preparing a histogram of the total signal intensities obtained by repeating the step a) for the remaining groups; and
   c) determining the presence of the target nucleic acid on the basis of the histogram pattern.

9. A method for detecting the presence of a target nucleic acid in a sample using an array substrate having plural probe spots, wherein said probe spots are arranged into groups such that each group contains probes not found in other groups, and the spots are grouped into two or more groups of two or more spots, the method comprising:
   a) measuring a total intensity of signals emitted from the probes in each group wherein the probes are in a hybridized state;
   b) preparing a histogram of signal intensities of the groups to obtain a pattern; and
   c) determining the presence of the target nucleic acid on the basis of the histogram pattern.

10. The method according to claim 9, wherein the groups comprise at least a first group and a second group, the signal intensity of the first group is strongest in hybridization with a first target nucleic acid, and the signal intensity of the second group is strongest in hybridization with a second target nucleic acid.

11. An array substrate for determining the presence or absence of a target nucleic acid in a sample, the array substrate comprising:
   a substrate;
   probe molecules; and
   a plurality of spots of probe molecules arranged on the substrate in an array form,
   wherein the probe molecules are the same in one probe spot and different between probe spots, and the probe spots are divided into plural regions, grouped such that each region contains probe molecules not found in other regions, and each region corresponds to one of target nucleic acids different in their sequence.

12. An array substrate for determining the presence of at least one of a first target nucleic acid and a second target nucleic acid in a sample, the array substrate comprising:
   a substrate;
   probe molecules; and
   a plurality of spots of probes arranged on the substrate in an array form, wherein the probe molecules are the same in one probe spot and different between probe spots, grouped such that each region contains probes not found in other regions, and the probe spots are grouped into groups of at least two or more probe spots, the first group is expected to give a stronger integral signal intensity in hybridization with a first target nucleic acid than with a second target nucleic acid, and the second group is expected to give a stronger integral signal intensity in hybridization with the second target nucleic acid than with the first target nucleic acid.

* * * * *

UNITED STATES PATENT AND TRADEMARK OFFICE
CERTIFICATE OF CORRECTION

PATENT NO.    : 6,924,103 B2                                              Page 1 of 1
DATED         : August 2, 2005
INVENTOR(S)   : Nobuko Yamamoto et al.

It is certified that error appears in the above-identified patent and that said Letters Patent is hereby corrected as shown below:

Column 6,
Line 54, "Further" should read -- Further, --.

Column 7,
Line 33, "connect" should read -- connect to --.

Column 8,
Line 17, "be" should be deleted.

Column 9,
Line 35, "continue" should read -- continued --.

Column 11,
Line 26, "is" should read -- as --; and
Line 51, "5'-Rho-ATGAACCAGAGGCCCATC-3'" should read -- 5'-Rho-ATGAACCAGAGGCCCATC-3' --.

Column 12,
Line 32, "No. 67: 5'-Rho-ATGAACCGGAGTCCCATC-3' (SEQ ID" should read -- No. 67: 5'-Rho-ATGAACCGGAGTCCCATC-3' --.

Signed and Sealed this

Fourteenth Day of February, 2006

JON W. DUDAS
*Director of the United States Patent and Trademark Office*

SEQUENCE LISTING

<160> NUMBER OF SEQ ID NOS: 67

<210> SEQ ID NO 1
<211> LENGTH: 18
<212> TYPE: DNA
<213> ORGANISM: Artificial sequence
<220> FEATURE:
<223> OTHER INFORMATION: Sample oligonucleotide

<400> SEQUENCE: 1
gatgggactc aagttcat                                                          18

<210> SEQ ID NO 2
<211> LENGTH: 18
<212> TYPE: DNA
<213> ORGANISM: Artificial sequence
<220> FEATURE:
<223> OTHER INFORMATION: Sample oligonucleotide

<400> SEQUENCE: 2
gatgggactc aggttcat                                                          18

<210> SEQ ID NO 3
<211> LENGTH: 18
<212> TYPE: DNA
<213> ORGANISM: Artificial sequence
<220> FEATURE:
<223> OTHER INFORMATION: Sample oligonucleotide

<400> SEQUENCE: 3
gatgggactc acgttcat                                                          18

<210> SEQ ID NO 4
<211> LENGTH: 18
<212> TYPE: DNA
<213> ORGANISM: Artificial sequence
<220> FEATURE:
<223> OTHER INFORMATION: Sample oligonucleotide

<400> SEQUENCE: 4
gatgggactc atgttcat                                                          18

<210> SEQ ID NO 5
<211> LENGTH: 18
<212> TYPE: DNA
<213> ORGANISM: Artificial sequence
<220> FEATURE:
<223> OTHER INFORMATION: Sample oligonucleotide

<400> SEQUENCE: 5
gatgggactc gagttcat                                                          18

<210> SEQ ID NO 6
<211> LENGTH: 18
<212> TYPE: DNA
<213> ORGANISM: Artificial sequence
<220> FEATURE:
<223> OTHER INFORMATION: Sample oligonucleotide

<400> SEQUENCE: 6
gatgggactc gggttcat                                                          18

<210> SEQ ID NO 7
<211> LENGTH: 18

```
<212> TYPE: DNA
<213> ORGANISM: Artificial sequence
<220> FEATURE:
<223> OTHER INFORMATION: Sample oligonucleotide

<400> SEQUENCE: 7
gatgggactc gcgttcat                                                 18

<210> SEQ ID NO 8
<211> LENGTH: 18
<212> TYPE: DNA
<213> ORGANISM: Artificial sequence
<220> FEATURE:
<223> OTHER INFORMATION: Sample oligonucleotide

<400> SEQUENCE: 8
gatgggactc gtgttcat                                                 18

<210> SEQ ID NO 9
<211> LENGTH: 18
<212> TYPE: DNA
<213> ORGANISM: Artificial sequence
<220> FEATURE:
<223> OTHER INFORMATION: Sample oligonucleotide

<400> SEQUENCE: 9
gatgggactc cagttcat                                                 18

<210> SEQ ID NO 10
<211> LENGTH: 18
<212> TYPE: DNA
<213> ORGANISM: Artificial sequence
<220> FEATURE:
<223> OTHER INFORMATION: Sample oligonucleotide

<400> SEQUENCE: 10
gatgggactc cggttcat                                                 18

<210> SEQ ID NO 11
<211> LENGTH: 18
<212> TYPE: DNA
<213> ORGANISM: Artificial sequence
<220> FEATURE:
<223> OTHER INFORMATION: Sample oligonucleotide

<400> SEQUENCE: 11
gatgggactc ccgttcat                                                 18

<210> SEQ ID NO 12
<211> LENGTH: 18
<212> TYPE: DNA
<213> ORGANISM: Artificial sequence
<220> FEATURE:
<223> OTHER INFORMATION: Sample oligonucleotide

<400> SEQUENCE: 12
gatgggactc ctgttcat                                                 18

<210> SEQ ID NO 13
<211> LENGTH: 18
<212> TYPE: DNA
<213> ORGANISM: Artificial sequence
<220> FEATURE:
<223> OTHER INFORMATION: Sample oligonucleotide

<400> SEQUENCE: 13
```
gatgggactc tagttcat                                                 18

<210> SEQ ID NO 14
<211> LENGTH: 18
<212> TYPE: DNA
<213> ORGANISM: Artificial sequence
<220> FEATURE:
<223> OTHER INFORMATION: Sample oligonucleotide

<400> SEQUENCE: 14
gatgggactc tggttcat                                                 18

<210> SEQ ID NO 15
<211> LENGTH: 18
<212> TYPE: DNA
<213> ORGANISM: Artificial sequence
<220> FEATURE:
<223> OTHER INFORMATION: Sample oligonucleotide

<400> SEQUENCE: 15
gatgggactc tcgttcat                                                 18

<210> SEQ ID NO 16
<211> LENGTH: 18
<212> TYPE: DNA
<213> ORGANISM: Artificial sequence
<220> FEATURE:
<223> OTHER INFORMATION: Sample oligonucleotide

<400> SEQUENCE: 16
gatgggactc ttgttcat                                                 18

<210> SEQ ID NO 17
<211> LENGTH: 18
<212> TYPE: DNA
<213> ORGANISM: Artificial sequence
<220> FEATURE:
<223> OTHER INFORMATION: Sample oligonucleotide

<400> SEQUENCE: 17
gatggggctc aagttcat                                                 18

<210> SEQ ID NO 18
<211> LENGTH: 18
<212> TYPE: DNA
<213> ORGANISM: Artificial sequence
<220> FEATURE:
<223> OTHER INFORMATION: Sample oligonucleotide

<400> SEQUENCE: 18
gatggggctc aggttcat                                                 18

<210> SEQ ID NO 19
<211> LENGTH: 18
<212> TYPE: DNA
<213> ORGANISM: Artificial sequence
<220> FEATURE:
<223> OTHER INFORMATION: Sample oligonucleotide

<400> SEQUENCE: 19
gatggggctc acgttcat                                                 18

<210> SEQ ID NO 20
<211> LENGTH: 18
<212> TYPE: DNA
<213> ORGANISM: Artificial sequence

```
<220> FEATURE:
<223> OTHER INFORMATION: Sample oligonucleotide

<400> SEQUENCE: 20
gatggggctc atgttcat                                                    18

<210> SEQ ID NO 21
<211> LENGTH: 18
<212> TYPE: DNA
<213> ORGANISM: Artificial sequence
<220> FEATURE:
<223> OTHER INFORMATION: Sample oligonucleotide

<400> SEQUENCE: 21
gatggggctc gagttcat                                                    18

<210> SEQ ID NO 22
<211> LENGTH: 18
<212> TYPE: DNA
<213> ORGANISM: Artificial sequence
<220> FEATURE:
<223> OTHER INFORMATION: Sample oligonucleotide

<400> SEQUENCE: 22
gatggggctc gggttcat                                                    18

<210> SEQ ID NO 23
<211> LENGTH: 18
<212> TYPE: DNA
<213> ORGANISM: Artificial sequence
<220> FEATURE:
<223> OTHER INFORMATION: Sample oligonucleotide

<400> SEQUENCE: 23
gatggggctc gcgttcat                                                    18

<210> SEQ ID NO 24
<211> LENGTH: 18
<212> TYPE: DNA
<213> ORGANISM: Artificial sequence
<220> FEATURE:
<223> OTHER INFORMATION: Sample oligonucleotide

<400> SEQUENCE: 24
gatggggctc gtgttcat                                                    18

<210> SEQ ID NO 25
<211> LENGTH: 18
<212> TYPE: DNA
<213> ORGANISM: Artificial sequence
<220> FEATURE:
<223> OTHER INFORMATION: Sample oligonucleotide

<400> SEQUENCE: 25
gatggggctc cagttcat                                                    18

<210> SEQ ID NO 26
<211> LENGTH: 18
<212> TYPE: DNA
<213> ORGANISM: Artificial sequence
<220> FEATURE:
<223> OTHER INFORMATION: Sample oligonucleotide

<400> SEQUENCE: 26
gatggggctc cggttcat                                                    18
```

```
<210> SEQ ID NO 27
<211> LENGTH: 18
<212> TYPE: DNA
<213> ORGANISM: Artificial sequence
<220> FEATURE:
<223> OTHER INFORMATION: Sample oligonucleotide

<400> SEQUENCE: 27
gatggggctc ccgttcat                                                 18

<210> SEQ ID NO 28
<211> LENGTH: 18
<212> TYPE: DNA
<213> ORGANISM: Artificial sequence
<220> FEATURE:
<223> OTHER INFORMATION: Sample oligonucleotide

<400> SEQUENCE: 28
gatggggctc ctgttcat                                                 18

<210> SEQ ID NO 29
<211> LENGTH: 18
<212> TYPE: DNA
<213> ORGANISM: Artificial sequence
<220> FEATURE:
<223> OTHER INFORMATION: Sample oligonucleotide

<400> SEQUENCE: 29
gatggggctc tagttcat                                                 18

<210> SEQ ID NO 30
<211> LENGTH: 18
<212> TYPE: DNA
<213> ORGANISM: Artificial sequence
<220> FEATURE:
<223> OTHER INFORMATION: Sample oligonucleotide

<400> SEQUENCE: 30
gatggggctc tggttcat                                                 18

<210> SEQ ID NO 31
<211> LENGTH: 18
<212> TYPE: DNA
<213> ORGANISM: Artificial sequence
<220> FEATURE:
<223> OTHER INFORMATION: Sample oligonucleotide

<400> SEQUENCE: 31
gatggggctc tcgttcat                                                 18

<210> SEQ ID NO 32
<211> LENGTH: 18
<212> TYPE: DNA
<213> ORGANISM: Artificial sequence
<220> FEATURE:
<223> OTHER INFORMATION: Sample oligonucleotide

<400> SEQUENCE: 32
gatggggctc ttgttcat                                                 18

<210> SEQ ID NO 33
<211> LENGTH: 18
<212> TYPE: DNA
<213> ORGANISM: Artificial sequence
<220> FEATURE:
<223> OTHER INFORMATION: Sample oligonucleotide
```

```
<400> SEQUENCE: 33
gatgggcctc aagttcat                                              18

<210> SEQ ID NO 34
<211> LENGTH: 18
<212> TYPE: DNA
<213> ORGANISM: Artificial sequence
<220> FEATURE:
<223> OTHER INFORMATION: Sample oligonucleotide

<400> SEQUENCE: 34
gatgggcctc aggttcat                                              18

<210> SEQ ID NO 35
<211> LENGTH: 18
<212> TYPE: DNA
<213> ORGANISM: Artificial sequence
<220> FEATURE:
<223> OTHER INFORMATION: Sample oligonucleotide

<400> SEQUENCE: 35
gatgggcctc acgttcat                                              18

<210> SEQ ID NO 36
<211> LENGTH: 18
<212> TYPE: DNA
<213> ORGANISM: Artificial sequence
<220> FEATURE:
<223> OTHER INFORMATION: Sample oligonucleotide

<400> SEQUENCE: 36
gatgggcctc atgttcat                                              18

<210> SEQ ID NO 37
<211> LENGTH: 18
<212> TYPE: DNA
<213> ORGANISM: Artificial sequence
<220> FEATURE:
<223> OTHER INFORMATION: Sample oligonucleotide

<400> SEQUENCE: 37
gatgggcctc gagttcat                                              18

<210> SEQ ID NO 38
<211> LENGTH: 18
<212> TYPE: DNA
<213> ORGANISM: Artificial sequence
<220> FEATURE:
<223> OTHER INFORMATION: Sample oligonucleotide

<400> SEQUENCE: 38
gatgggcctc gggttcat                                              18

<210> SEQ ID NO 39
<211> LENGTH: 18
<212> TYPE: DNA
<213> ORGANISM: Artificial sequence
<220> FEATURE:
<223> OTHER INFORMATION: Sample oligonucleotide

<400> SEQUENCE: 39
gatgggcctc gcgttcat                                              18

<210> SEQ ID NO 40
```

```
<211> LENGTH: 18
<212> TYPE: DNA
<213> ORGANISM: Artificial sequence
<220> FEATURE:
<223> OTHER INFORMATION: Sample oligonucleotide

<400> SEQUENCE: 40
gatgggcctc gtgttcat                                                 18

<210> SEQ ID NO 41
<211> LENGTH: 18
<212> TYPE: DNA
<213> ORGANISM: Artificial sequence
<220> FEATURE:
<223> OTHER INFORMATION: Sample oligonucleotide

<400> SEQUENCE: 41
gatgggcctc cagttcat                                                 18

<210> SEQ ID NO 42
<211> LENGTH: 18
<212> TYPE: DNA
<213> ORGANISM: Artificial sequence
<220> FEATURE:
<223> OTHER INFORMATION: Sample oligonucleotide

<400> SEQUENCE: 42
gatgggcctc cggttcat                                                 18

<210> SEQ ID NO 43
<211> LENGTH: 18
<212> TYPE: DNA
<213> ORGANISM: Artificial sequence
<220> FEATURE:
<223> OTHER INFORMATION: Sample oligonucleotide

<400> SEQUENCE: 43
gatgggcctc ccgttcat                                                 18

<210> SEQ ID NO 44
<211> LENGTH: 18
<212> TYPE: DNA
<213> ORGANISM: Artificial sequence
<220> FEATURE:
<223> OTHER INFORMATION: Sample oligonucleotide

<400> SEQUENCE: 44
gatgggcctc ctgttcat                                                 18

<210> SEQ ID NO 45
<211> LENGTH: 18
<212> TYPE: DNA
<213> ORGANISM: Artificial sequence
<220> FEATURE:
<223> OTHER INFORMATION: Sample oligonucleotide

<400> SEQUENCE: 45
gatgggcctc tagttcat                                                 18

<210> SEQ ID NO 46
<211> LENGTH: 18
<212> TYPE: DNA
<213> ORGANISM: Artificial sequence
<220> FEATURE:
<223> OTHER INFORMATION: Sample oligonucleotide

<400> SEQUENCE: 46
```

```
gatgggcctc tggttcat                                              18

<210> SEQ ID NO 47
<211> LENGTH: 18
<212> TYPE: DNA
<213> ORGANISM: Artificial sequence
<220> FEATURE:
<223> OTHER INFORMATION: Sample oligonucleotide

<400> SEQUENCE: 47
gatgggcctc tcgttcat                                              18

<210> SEQ ID NO 48
<211> LENGTH: 18
<212> TYPE: DNA
<213> ORGANISM: Artificial sequence
<220> FEATURE:
<223> OTHER INFORMATION: Sample oligonucleotide

<400> SEQUENCE: 48
gatgggcctc ttgttcat                                              18

<210> SEQ ID NO 49
<211> LENGTH: 18
<212> TYPE: DNA
<213> ORGANISM: Artificial sequence
<220> FEATURE:
<223> OTHER INFORMATION: Sample oligonucleotide

<400> SEQUENCE: 49
gatgggtctc aagttcat                                              18

<210> SEQ ID NO 50
<211> LENGTH: 18
<212> TYPE: DNA
<213> ORGANISM: Artificial sequence
<220> FEATURE:
<223> OTHER INFORMATION: Sample oligonucleotide

<400> SEQUENCE: 50
gatgggtctc aggttcat                                              18

<210> SEQ ID NO 51
<211> LENGTH: 18
<212> TYPE: DNA
<213> ORGANISM: Artificial sequence
<220> FEATURE:
<223> OTHER INFORMATION: Sample oligonucleotide

<400> SEQUENCE: 51
gatgggtctc acgttcat                                              18

<210> SEQ ID NO 52
<211> LENGTH: 18
<212> TYPE: DNA
<213> ORGANISM: Artificial sequence
<220> FEATURE:
<223> OTHER INFORMATION: Sample oligonucleotide

<400> SEQUENCE: 52
gatgggtctc atgttcat                                              18

<210> SEQ ID NO 53
<211> LENGTH: 18
<212> TYPE: DNA
```

```
<213> ORGANISM: Artificial sequence
<220> FEATURE:
<223> OTHER INFORMATION: Sample oligonucleotide

<400> SEQUENCE: 53
gatgggtctc gagttcat                                                   18

<210> SEQ ID NO 54
<211> LENGTH: 18
<212> TYPE: DNA
<213> ORGANISM: Artificial sequence
<220> FEATURE:
<223> OTHER INFORMATION: Sample oligonucleotide

<400> SEQUENCE: 54
gatgggtctc gggttcat                                                   18

<210> SEQ ID NO 55
<211> LENGTH: 18
<212> TYPE: DNA
<213> ORGANISM: Artificial sequence
<220> FEATURE:
<223> OTHER INFORMATION: Sample oligonucleotide

<400> SEQUENCE: 55
gatgggtctc gcgttcat                                                   18

<210> SEQ ID NO 56
<211> LENGTH: 18
<212> TYPE: DNA
<213> ORGANISM: Artificial sequence
<220> FEATURE:
<223> OTHER INFORMATION: Sample oligonucleotide

<400> SEQUENCE: 56
gatgggtctc gtgttcat                                                   18

<210> SEQ ID NO 57
<211> LENGTH: 18
<212> TYPE: DNA
<213> ORGANISM: Artificial sequence
<220> FEATURE:
<223> OTHER INFORMATION: Sample oligonucleotide

<400> SEQUENCE: 57
gatgggtctc cagttcat                                                   18

<210> SEQ ID NO 58
<211> LENGTH: 18
<212> TYPE: DNA
<213> ORGANISM: Artificial sequence
<220> FEATURE:
<223> OTHER INFORMATION: Sample oligonucleotide

<400> SEQUENCE: 58
gatgggtctc cggttcat                                                   18

<210> SEQ ID NO 59
<211> LENGTH: 18
<212> TYPE: DNA
<213> ORGANISM: Artificial sequence
<220> FEATURE:
<223> OTHER INFORMATION: Sample oligonucleotide

<400> SEQUENCE: 59
gatgggtctc ccgttcat                                                   18
```

<210> SEQ ID NO 60
<211> LENGTH: 18
<212> TYPE: DNA
<213> ORGANISM: Artificial sequence
<220> FEATURE:
<223> OTHER INFORMATION: Sample oligonucleotide

<400> SEQUENCE: 60
gatgggtctc ctgttcat                                          18

<210> SEQ ID NO 61
<211> LENGTH: 18
<212> TYPE: DNA
<213> ORGANISM: Artificial sequence
<220> FEATURE:
<223> OTHER INFORMATION: Sample oligonucleotide

<400> SEQUENCE: 61
gatgggtctc tagttcat                                          18

<210> SEQ ID NO 62
<211> LENGTH: 18
<212> TYPE: DNA
<213> ORGANISM: Artificial sequence
<220> FEATURE:
<223> OTHER INFORMATION: Sample oligonucleotide

<400> SEQUENCE: 62
gatgggtctc tggttcat                                          18

<210> SEQ ID NO 63
<211> LENGTH: 18
<212> TYPE: DNA
<213> ORGANISM: Artificial sequence
<220> FEATURE:
<223> OTHER INFORMATION: Sample oligonucleotide

<400> SEQUENCE: 63
gatgggtctc tcgttcat                                          18

<210> SEQ ID NO 64
<211> LENGTH: 18
<212> TYPE: DNA
<213> ORGANISM: Artificial sequence
<220> FEATURE:
<223> OTHER INFORMATION: Sample oligonucleotide

<400> SEQUENCE: 64
gatgggtctc ttgttcat                                          18

<210> SEQ ID NO 65
<211> LENGTH: 18
<212> TYPE: DNA
<213> ORGANISM: p53 fragment
<220> FEATURE:
<223> OTHER INFORMATION: Sample oligonucleotide

<400> SEQUENCE: 65
atgaaccgga ggcccatc                                          18

<210> SEQ ID NO 66
<211> LENGTH: 18
<212> TYPE: DNA
<213> ORGANISM: Artificial sequence
<220> FEATURE:

```
-continued

<223> OTHER INFORMATION: Sample oligonucleotide

<400> SEQUENCE: 66
atgaaccaga ggcccatc                                                       18

<210> SEQ ID NO 67
<211> LENGTH: 18
<212> TYPE: DNA
<213> ORGANISM: Artificial sequence
<220> FEATURE:
<223> OTHER INFORMATION: Sample oligonucleotide

<400> SEQUENCE: 67
atgaaccgga gtcccatc                                                       18
```